United States Patent [19]

Tremulis

[11] Patent Number: 4,731,056
[45] Date of Patent: Mar. 15, 1988

[54] EXTERNAL DRAINAGE ANTISIPHON DEVICE

[75] Inventor: William S. Tremulis, Newport Beach, Calif.

[73] Assignee: Cordis Corporation, Miami, Fla.

[21] Appl. No.: 935,105

[22] Filed: Nov. 24, 1986

Related U.S. Application Data

[63] Continuation of Ser. No. 703,022, Feb. 19, 1985, abandoned.

[51] Int. Cl.$^4$ .............................................. A61M 1/00
[52] U.S. Cl. .................................... 604/118; 604/128; 604/326
[58] Field of Search ......... 604/9, 10, 27, 30, 127–129, 604/247, 246, 317, 326, 118; 137/533.11, 131; 73/861.55, 861.57

[56] References Cited

U.S. PATENT DOCUMENTS

| | | | |
|---|---|---|---|
| 523,739 | 7/1894 | Fleiner | 137/131 |
| 720,100 | 2/1903 | Bashlin | 137/533.11 |
| 2,879,784 | 3/1959 | Cutter | 604/127 |
| 3,183,713 | 5/1965 | Gilmont | 73/861.55 |
| 3,957,050 | 5/1976 | Hines, Jr. | 604/246 |
| 4,332,255 | 6/1982 | Hakim et al. | 604/9 |

Primary Examiner—Dalton L. Truluck
Assistant Examiner—J. L. Kruter
Attorney, Agent, or Firm—Henry W. Collins; Thomas R. Vigil

[57] ABSTRACT

The ventricular drainage system includes an antisiphon device comprising a flow through body which has an interior chamber and which is adapted to be positioned for vertical flow therethrough. The device further includes an inflow tract at the lower end of the body, adapted to be coupled to a ventricular catheter, and an outflow tract at the upper end of said body adapted to be coupled to a drainage tubing. The device also includes a ball in the chamber which is capable of closing the inflow tract when there is no flow of fluid from the ventricular catheter, capable of allowing fluid flow through the body during normal flow of liquid from the catheter and capable of closing the outflow tract upon a rush of fluid from the catheter.

15 Claims, 6 Drawing Figures

EXTERNAL DRAINAGE ANTISIPHON DEVICE

This is a continuation of application Ser. No. 703,022, filed Feb. 19, 1985, now abandoned.

BACKGROUND OF THE INVENTION

1. Field of the Invention

The present invention relates to an apparatus for externally draining fluid from a body, in particular cerebral spinal fluid from a brain, which includes an antisiphon device that is capable of preventing reflux of fluid while allowing fluid to flow out of the brain and that is capable of preventing excessive fluid flow during mishandling.

2. Description of the Prior Art

Heretofore, various external ventricular draining apparatus and external ventricular monitoring and draining apparatus have been proposed. Such apparatus includes a ventricular catheter whose distal end is placed in the ventricle of the brain of a patient. This apparatus relies on a siphon created by gravity to drain excess fluid from the ventricle.

The ventricular catheter described above has a proximal end which has a luer connector attached to it. The luer connector is in turn connected to a connector on one end of a piece of tubing. The tubing is normal surgical fluid tubing and extends a short distance into the top of a drip chamber. The drip chamber is normally positioned in a vertical plane and is a device commonly used in fluid drainage by doctors and nurses. The bottom end of the drip chamber has a connector which accommodates surgical tubing.

Frequently, tubing is connected to the bottom of the drip chamber and travels a short distance downward with respect to gravity and is sometimes connected to a stopcock for sampling of the cerebral fluid. This stopcock has connectors means at both ends to accommodate surgical tubing which runs a the valve from the drip chamber and then out of the valve and downward a short distance to a drainage bag. This bag is normally a common plastic bag used to accumulate cerebral fluid. The bag readily connects to the surgical tubing to allow replacement when full.

In operation, the apparatus is clamped to a pole such as an I.V. pole and placed at a height relative to the height of the brain of a patient which will allow gravity to remove any excess cerebral fluid. Drainage occurs when the pressure of the body fluid exceeds the pressure determined by the height of the drainage apparatus relative to the height of the patient's brain. This height is critical since it must be positioned to only allow drainage of excess cerebral fluid. If the height of the system is too high, the pressure of the system is greater than that of the fluid pressure in the patient's body and reverse flow will occur. If the height of the system is too low, the system acts as a siphon and too much fluid is drained from the patient which can cause severe injury to a patient.

It is possible through accident, mishandling of the system or other uncontrolled events that the height of the system does fall drastically below the height of the patient's brain. Therefore, it is desirable to provide such a system with a device which will prevent any mishandling or error in the set-up and use of the external drainage system to prevent injury to a patient.

As will be described in greater detail hereinafter, the apparatus of the present invention differs from the apparatus previously proposed by providing an antisiphon device contained within an external drainage system as described above and positioned between a ventricular catheter and a drip chamber in a vertical plane.

As described in greater detail hereinafter, the antisiphon device is elongated and has openings at each end with a connector and being sized to accommodate surgical tubing from the ventricular catheter with a connector at the top end having an outflow tract therein and being capable of connecting to the drip chamber.

This antisiphon device is constructed in such a way so that in cases of no flow from the brain of a patient, the inflow tract is closed preventing reflux of fluid. Additionally, the device is constructed in such a way so that in cases of normal fluid flow from the brain, the inflow tract is open and fluid is allowed to pass freely into and through the antisiphon device and out the outflow tract, into the drip chamber.

Finally, the device is constructed in such a way so that in the event the height of the system drastically falls below the height of the brain of the patient, which will cause excessive flow, the outflow tract of the device is blocked which prevents fluid flow as well as excess drainage and damage to the patient.

SUMMARY OF THE INVENTION

The invention provides an external ventricular drainage apparatus. The apparatus comprises a ventricular catheter and an antisiphon device. The antisiphon device includes an elongate body having an interior chamber therein, an inflow tract at one end of the body communicating with the chamber and an outflow tract communicating with the other end of the chamber. The body is positioned in a generally upright position with the outflow tract being located above the inflow tract. Movable means, such as a ball, is situated in the chamber for sealing the inflow and the outflow tracts during differing flow patterns through the elongate body. Means are provided for connecting the catheter to the inflow tract of the antisiphon device. The apparatus further includes a drip chamber, a drainage bag, means for connecting the outflow tract of the antisiphon to the drip chamber and means for connecting the drip chamber to the drainage bag.

DESCRIPTION OF THE PREFERRED EMBODIMENT

Figure 1:
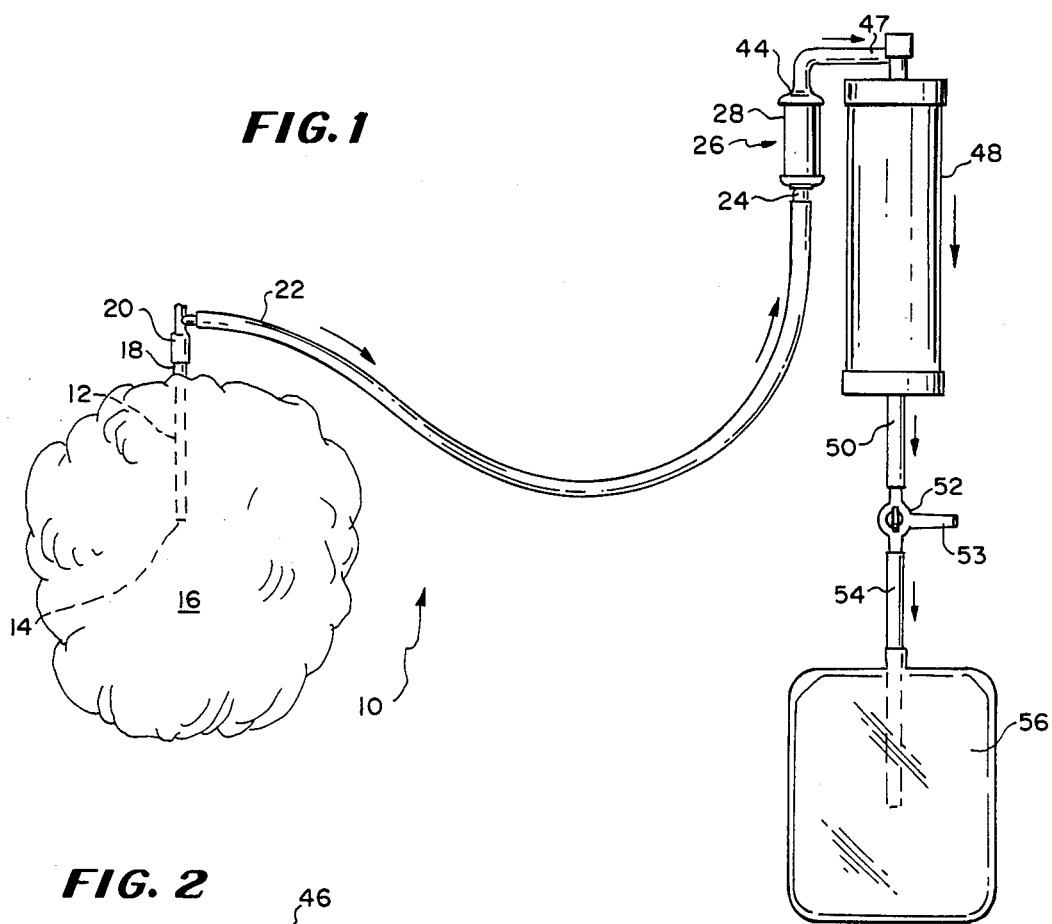
FIG. 1 is a plan view of an external ventricular drainage apparatus constructed according to the teachings of the present invention.

Referring now to the drawings in greater detail, there is illustrated in FIG. 1 an external ventricular drainage apparatus 10 constructed according to the teachings of the present invention.

The drainage apparatus 10 includes a ventricular catheter 12 having a distal end 14 inserted into a ventricle of a brain 16 of a patient, and has attached to its proximal end 18, a luer connector 20.

The luer connector 20 has a piece of tubing 22 attached to an end thereof opposite the ventricular catheter 12. This tubing 22 can be of any type which is flexible and will allow drainage, such as an ordinary surgical plastic tubing.

This tube 22 extends a short distance away from the patient and is attached to a connector 24 of an antisiphon device 26 constructed according to the teachings of the present invention which regulates fluid flow through the drainage apparatus 10. The antisiphon device 26 is adapted to be positioned vertically as shown.

Figure 3A:
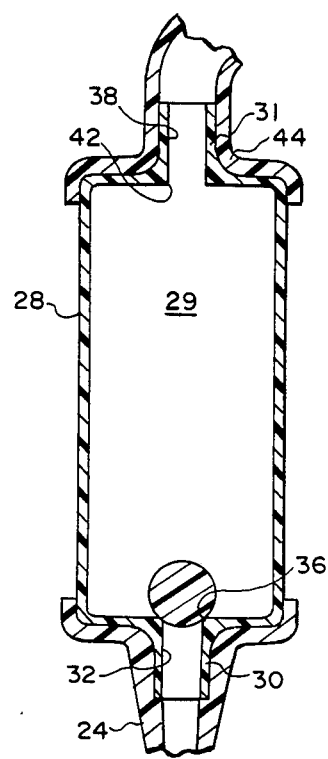
FIG. 3A is a vertical sectional view of the antisiphon device shown in FIG. 2 and shows the device in a no flow period.

As best shown in FIG. 3A, the antisiphon device 26 comprises an elongate body 28 which is constructed of a clear thermoplastic such as polyvinylchloride or polycarbonate. The body 28 has an interior chamber 29 and a nipple 30 at a lower end and a nipple 31 at the upper end as shown.

The antisiphon device 26 has an inflow tract 32 in the nipple 30, with a valve seat 36 being defined at the opening of the tract 32 into the chamber 29. The antisiphon device also has an outflow tract 38 in the nipple 31, with a valve seat 42 defined at the opening of the tract 38 into the chamber 29.

Figure 2:
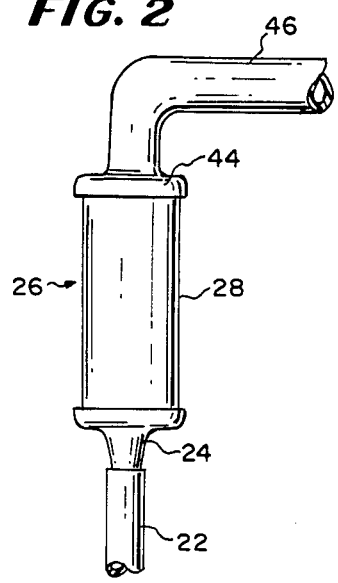
FIG. 2 is a vertical elevational view of an antisiphon device of the present invention used in the apparatus shown in FIG. 1.

The connector 24 is received over and bonded to the nipple 30 by appropriate bonding means. Similarly, a cap 44 at the lower end of a rigid hollow sidearm 46 is received over and fixed to the nipple 40. An upper end 47 of the sidearm 46 is coupled to a drip chamber 48 which holds the antisiphon device parallel to the drip chamber 48 which in turn is mounted in a generally vertical position as illustrated in FIGS. 1, 2 and 3A.

A tubing 50 at the lower end of the drip chamber 48 is connected to a stopcock 52 which has a tap 53 and a lower end coupled to a tubing 54 that extends into a removable and replaceable drainage bag 56.

Figure 3B:
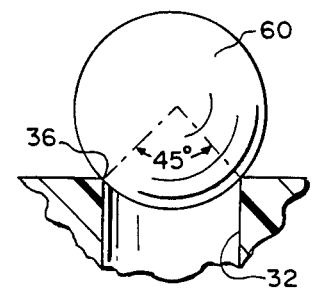
FIG. 3B is a fragmentary vertical sectional view of the antisiphon device shown in FIG. 3A and shows the angle subtended by a ball seated on a valve seat.

As illustrated in FIG. 3B, the antisiphon device 26 further includes a synthetic sapphire ball 60 in the chamber 29. The chamber 29 is larger-in-diameter than the tracts 32 and 38; and the openings at valve seats 36 and 42 and the ball 60 are sized so that a spherical segment acting on either valve seat 36 or 42 subtends a 45 degree angle at the center of the ball 60. This permits the ball 60 to close the respective inflow or outflow tracts 32 and 38 when the ball 60 comes in contact with one of the valve seats 36 or 42. In operation, the ball 60 of the antisiphon device 26 can be in one of several different positions.

In those situations in which the pressure of the cerebral spinal fluid in the ventricles of the brain 16 is equal to or less than the pressure determined by the position of the drainage apparatus 10 there is no fluid flow. In this instance, the ball 60 of the antisiphon device 26 is positioned on the valve seat 36 and prevents fluid flow back into the inflow tract 32 as shown in FIG. 3A.

Figure 4:
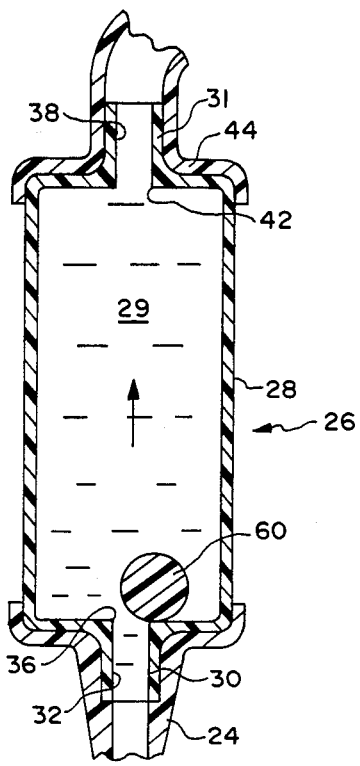
FIG. 4 is a vertical sectional view of the antisiphon device, similar to the view shown in FIG. 3A, and shows the device during a period of normal low fluid flow.

When the pressure of the cerebral spinal fluid in the ventricles of the brain 16 is greater than the pressure determined by the position of the drainage apparatus 10, there is fluid flow in the direction of the arrow in FIG. 4. In this instance, the cerebral spinal fluid displaces the ball 60 from the valve seat 36 and inflow tract 32 is no longer blocked. During periods of flow, the ball 60 can be in any position within the elongate body 28.

Figure 5:
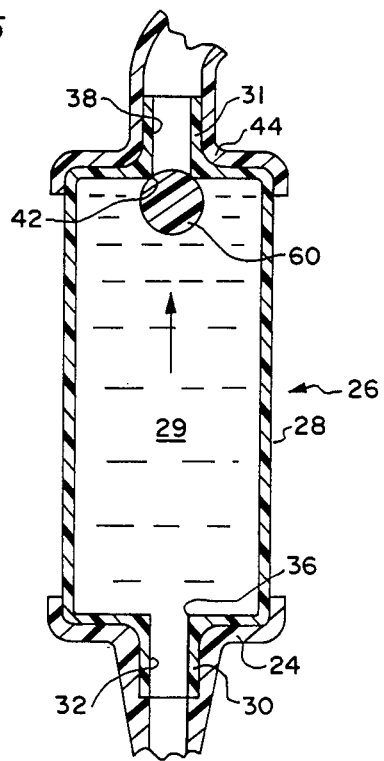
FIG. 5 is a vertical sectional view of the antisiphon device, similar to the view shown in FIG. 4 during a period of high fluid flow.

If there is an accidental dropping of the drainage apparatus 10 causing the pressure of the cerebral spinal fluid in the ventricles of the brain 16 to be much greater than the pressure determined by the position of the drainage apparatus 10, (or some other occurrence that would bring about a high flow of cerebral spinal fluid out of the brain 16), the ball 60 will be forced against valve seat 42 thereby blocking outflow tract 38 and preventing excess cerebral spinal fluid drainage as shown in FIG. 5.

When the pressure of the ventricles is equal to or less than the pressure determined by the position of the drainage apparatus 10, there is no fluid flow and, therefor, no fluid pattern. On these occasions, when the ventricular pressure is greater than the pressure in the drainage apparatus 10, the fluid flow, or the flow pattern, is from the ventricle to the drainage apparatus 10. In accidental lowering of the drainage apparatus 10, resulting in decreased pressure on the drainage apparatus 10 fluid flow or the flow pattern, is also from the ventricles to the drainage apparatus 10, but would result in collapse of the brain because of the rapid excess of fluid loss from the ventricles. This fluid loss is prevented by the ball 60 being forced against the valve seat 42 thereby blocking the outflow track 38.

When the height of the drainage apparatus 10 is returned to the proper height, the ball 60 no longer blocks outflow tract 38 and fluid flow is returned to normal.

After the fluid leaves the antisiphon device 26 through outflow tract 38, it proceeds through the sidearmn 46 into the drip chamber 48. Thereafter, the cerebral spinal fluid proceeds through the tube 50 to the stopcock 52 which allows an attendant to take samples of the fluid from tap 53. Finally, the fluid flows from the stopcock 52 through the piece of tubing 54 into the drainage bag 56.

Although one form of an external ventricular drainage apparatus 10 and antisiphon device 26 has been described above and illustrated in the drawings, it is to be understood that modifications can be made to the apparatus 10 and device 26 of the present invention without departing from the teachings of the invention. For example, the shape and size of the antisiphon device 26 can be varied as well as the material used. Accordingly, the scope of the invention is only to be limited as necessitated by the accompanying claims.

I claim:

1. An external ventricular drainage apparatus comprising:
   a ventricular catheter;
   an antisiphon device comprising an elongated body having an interior chamber therein, an inflow tract and valve seat at one end of said body communicating with said chamber, an outflow tract communicating with other end of said chamber, said body being positioned in a generally upright position with said outflow tract and valve seat being located above said inflow tract and movabale means in said chamber for sealing said inflow and said outflow tracts during differing flow patterns through said elongate body such that upon excess pressure said moveable means seals off said outflow tract at a position above said inflow tract valve seat;

means for connecting said catheter to said inflow tract of said antisiphon device;

a drip chamber;

means for connecting said outflow tract of said antisiphon to said drip chamber;

a drainage bag; and means for connecting said drip chamber to said drainage bag.

2. The apparatus of claim 1, wherein said elongate body of said antisiphon device is made of clear thermoplastic.

3. The apparatus of claim 1, wherein said movable means comprises a ball.

4. The apparatus of claim 1 wherein said chamber has an opening at each end communicating with one of said tracts.

5. The apparatus of claim 1, wherein said connecting means comprise surgical plastic tubing.

6. A ventricular drainage apparatus including draingae means for draining a ventricle in a brain and an antisiphon device, said antisiphon device comprising:

an elongate body having an interior flowthrough chamber, said elongate body having first and second ends and being positioned generally upright with said second end above said first end;

a first upstream flow tract at said first end of said elongate body communicating with said interior flowthrough chamber and being coupled to said drainge means;

a first valve seat in said body at said first end of said chamber;

said first flow tract opening into said first end of said flowthrough chamber through said first valve seat;

a second valve seat in said body at said second end of said chamber;

said second flow tract opening into second end of said flowthrough chamber through said second valve seat; and movable means for sealing said first and said second valve seats during differing flow patterns through said interior flowthrough chamber of said elongate body thereby to prevent siphoning flow through said second flow tract.

7. The device of claim 6, wherein said body is made of clear thermoplastic.

8. The device of claim 6, wherein said movable means comprise a ball.

9. In a ventricular drainage system, comprising ventricular drainage means including a ventricular catheter and a drainage tubing,the improvement resaiding in an antisiphon device which is constructed and arranged to alow drainage of cerebrospinal fluid from the ventricles of the brain through the drainage tubing, and to prevent rapid siphoning of cerebrospinal fluid during accidental movement of the ventricular drainage means, said device comprising:

a flowthrough body adapted to be positioned generally upright for generally vertical upward flow of cerebrospinal fluid therethrough;

an inflow tract at the lower end of said body, said inflow tract being adapted to be coupled to the ventricular catheter;

an outflow tract at the upper end of said body, said outflow tract being adapted to be coupled to the drainage tubing; and movable means within said body capable of sealing said inflow tract when there is no flow of cerebrospinal fluid from the ventricular catheter, of allowing cerebrospinal fluid flow through said inflow tract during normal flow of cerebrospinal fluid from the catheter to the drainage tubing and of sealing said outflow tract upon a siphoning flow of cerebrospinal fluid from the catheter.

10. In a ventricle drainage system, comprising ventricular drainage means including a ventricular catheter and a drainage tubing, and a drainage bag connected by said tubing to said catheter, and improvement residing in an antisiphon device which is constructed and arranged to allow drainage of cerebrospinal fluid from the ventricles of the brain through the drainage tubing and antisiphon device to the bag, and to prevent rapid siphoning of cerebrospinal fluid during accidental movement of the ventricular drainage means, said device comprising:

a flow-through body adapted to be positioned generally upright for generally vertical upward flow of cerebospinal fluid therethrough;

an inflow tract at the lower end of said body, said inflow tract being adapted to be coupled to the ventricular catheter;

an outflow tract at the upper end of said body, said outflow tract beign adapted to be coupled to the drainage tubing;

said body having an interior chamber therein larger-in-cross sectional area than the cross-sectional area of said inflow tract or the cross-sectional area of said outflow tract; and movable means within said body freely movable within said chamber and having a cross-sectional area larger than the cross-sectional area of said inflow and said outflow tracts upon a siphoning flow of cerebrospinal fluid into said chamber.

11. The device of claim 10 wherein said movable means is a ball.

12. The device of claim 11 wherein and ball is made of synthetic sapphire.

13. The device of claim 11 wherein said ball has a semi-spherical segment which is adaptd to cover said inflow tract or to cover said outflow tract to prevent the flow of cerebrospinal fluid.

14. The apparatus of claim 4 wherein said ball has a semi-spherical segment which when seated in one of said openings of said tracts, seals said opening.

15. The device of claim 6 wherein movable means for sealing said first or second valve seats comprise a spherical segment of said ball seated on said first or second valve seat.

* * * * *